(12) United States Patent  
Patt

(10) Patent No.: US 6,405,599 B1
(45) Date of Patent: Jun. 18, 2002

(54) FRICTIONLESS MOTOR MATERIAL TESTING

(75) Inventor: Paul J. Patt, Northborough, MA (US)

(73) Assignee: Bose Corporation, Framingham, MA (US)

(*) Notice: Subject to any disclaimer, the term of this patent is extended or adjusted under 35 U.S.C. 154(b) by 0 days.

(21) Appl. No.: 09/482,248

(22) Filed: Jan. 13, 2000

(51) Int. Cl.[7] .................................................. G01B 5/00
(52) U.S. Cl. ........................................................ 73/779
(58) Field of Search .......................... 73/763, 774, 776, 73/779, 796, 817; 318/11, 122

(56) References Cited

U.S. PATENT DOCUMENTS

| | | | |
|---|---|---|---|
| 3,746,937 A | * | 7/1973 | Koike .......................... 318/122 |
| 3,794,865 A | * | 2/1974 | Guttinger ....................... 310/82 |
| 4,675,615 A | * | 6/1987 | Bramanti ........................ 330/8 |
| 4,726,227 A | * | 2/1988 | Moffatt et al. ................ 73/505 |
| 5,216,723 A | * | 6/1993 | Froeschle et al. ........... 381/201 |

* cited by examiner

Primary Examiner—Max Noori
(74) Attorney, Agent, or Firm—Fish & Richardson P.C.

(57) ABSTRACT

A materials testing device including a frictionless suspension that operates without sliding contact between an armature assembly and the suspension. The disclosure describes materials testing device that includes a moving magnet linear motor and a flexural suspension which is mounted using a thin layer of acrylic adhesive.

25 Claims, 5 Drawing Sheets

FRICTIONLESS MOTOR MATERIAL TESTING

CROSS-REFERENCE TO RELATED APPLICATIONS

Not Applicable

STATEMENT REGARDING FEDERALLY SPONSORED RESEARCH OR DEVELOPMENT

Not Applicable

The invention relates to materials testing systems, and more particularly to frictionless suspending in materials testing systems.

It is an important object of the invention to provide a materials testing system having an improved suspension.

BRIEF SUMMARY OF THE INVENTION

According to the invention, a materials testing device for applying force to a test specimen includes a linear motor which includes an armature assembly which is mechanically coupleable to the test specimen, and a stator assembly. The materials testing device further includes a suspension for supporting the armature and for controlling the motion of the armature relative to the stator and to the test specimen, the suspension being arranged and constructed to operate without sliding contact between the armature assembly and the suspension.

In another aspect of the invention, a materials testing device includes a core of low reluctance magnetic material having two mutually opposing faces and an air gap separating the mutually opposing faces. A coil is wound around the core. A permanent magnet assembly is positioned in and substantially fills the air gap in noncontacting relationship with the core. The materials testing device further includes a frictionless flexural suspension structure for supporting the permanent magnet assemblPy and for controlling the direction of motion of the permanent magnet assembly.

In still another aspect of the invention, an electromechanical actuator assembly includes a structure of low reluctance material, a coil wound on the structure, the structure having substantially planar opposing faces. An air gap is between the opposing faces. A movable permanent magnet assembly having regions of opposite polarity is disposed in and substantially fills the air gap. The actuator assembly is characterized by three axes, a first of the axes perpendicular to the opposing faces, a second of the axes perpendicular to the first axis and between the regions of opposite polarity, a third of the axes perpendicular to the first axis and the second axis. A substantially frictionless suspension assembly supports the permanent magnet assembly. The suspension assembly has different stiffnesses along each of the three axes. The suspension is stiffest along the first axis.

Other features, objects, and advantages will become apparent from the following detailed description, which refers to the following drawings in which:

DETAILED DESCRIPTION

Figure 1:
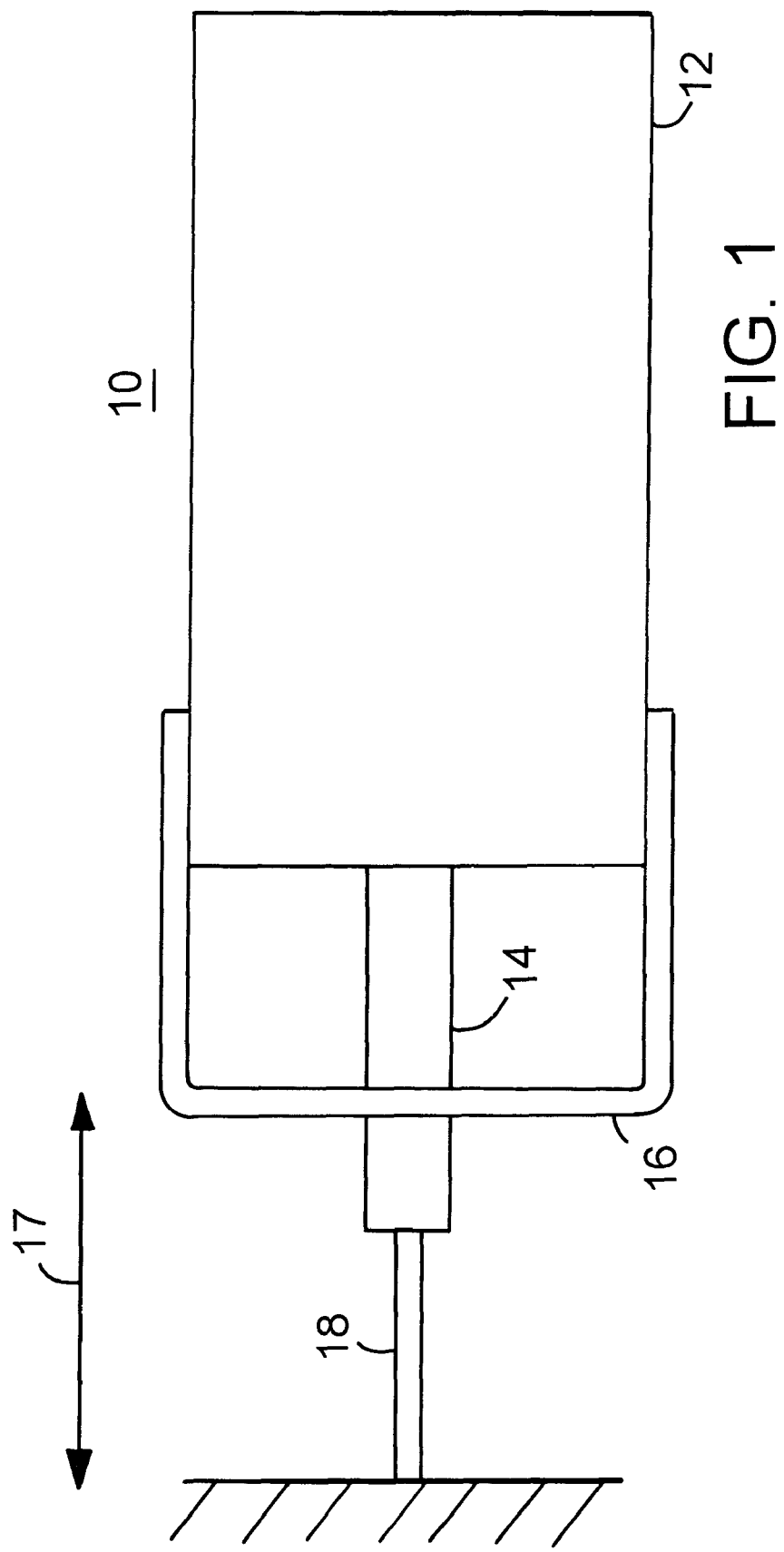
FIG. 1 is a diagrammatic view of a materials testing system according to the invention.

With reference now to the drawings and more particularly to FIG. 1, there is shown a materials testing system according to the invention. Linear motor 10 includes a stator assembly 12 and an armature 14. Frictionless flexural suspension element 16 supports and controls the motion of armature 14 without any sliding contact between moving elements and stationary elements. Armature 14 is mechanically coupled to test fixture 18. In operation, armature 14 moves along an axis indicated by arrow 17 and applies a force to test specimen 18, either inducing motion or mechanical stress, or both, in test specimen 18.

Linear motor 10, stator assembly 12, armature 14, and frictionless flexural suspension system 16 will be shown in more detail in subsequent figures and described in corresponding sections of the disclosure. The mechanical attachment between linear armature 14 and test specimen 18 may be conventional. The configuration of the test specimen is dependent on the specific materials test to be performed. Test specimen 18 may also be a test jig or fixture.

Figure 2:
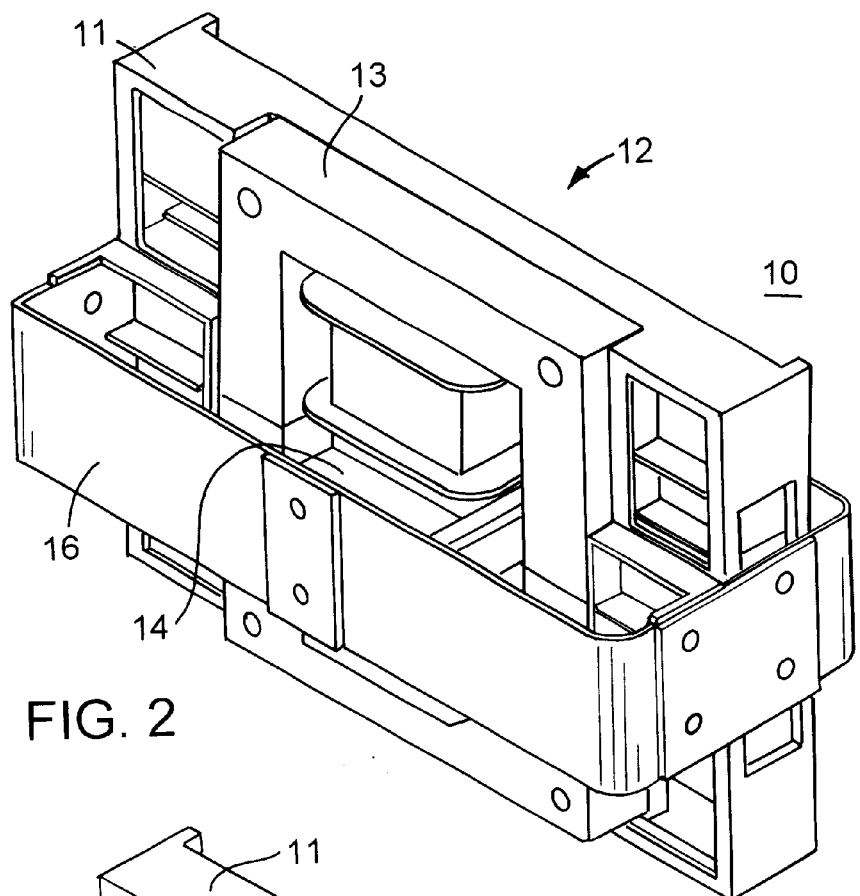
FIG. 2 is an isometric view of a linear motor assembly according to the invention.

Referring now to FIG. 2, there is shown a linear motor 10 with a frictionless flexural suspension element 16 according to the invention. Stator assembly 12 includes a frame 11 to which core portion 13 is mechanically attached. Frame 11 serves as an element which provides convenient coupling of core portion 13 and other elements of linear motor 10. Other embodiments of stator assembly 12 may not require frame 11. Frictionless flexural suspension system 16 holds armature 14 in position relative to other linear motor elements and controls the motion of armature 14 and may exert a restorative force along the direction of motion of armature 14. The direction of motion of armature 14 will be discussed below.

Figure 3:
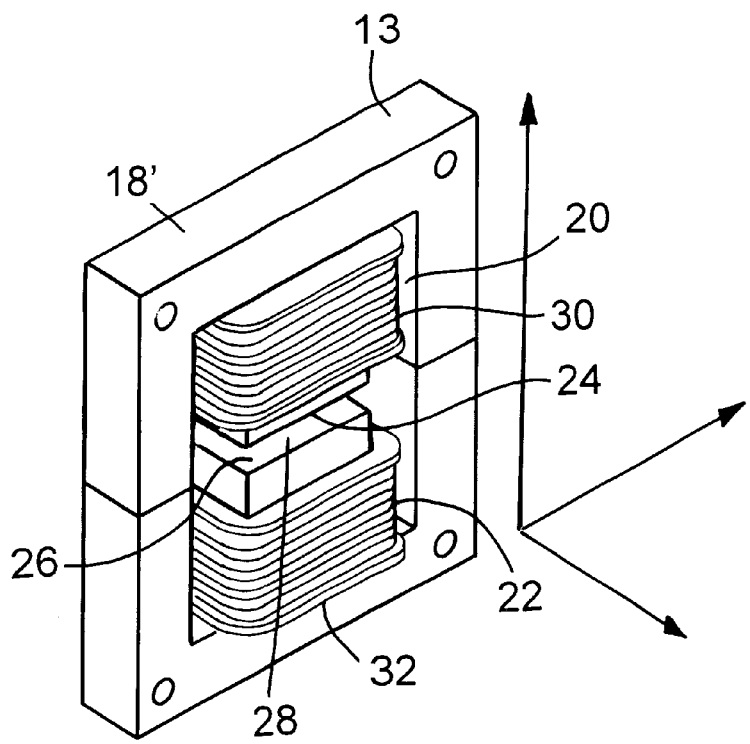
FIG. 3 is an isometric view of the core portion of the linear motor assembly of FIG. 2.

Referring to FIG. 3, there is shown core portion 13. Core portion 13 is made of a low reluctance material such as iron, and may be shaped with an outer portion 18'. Protruding inwardly from opposite sides of outer portion 18' may be two central core portions 20 and 22, which terminate in opposing faces 24, 26 respectively, separated by air gap 28. Coils 30, 32 are wrapped around central core portion 13.

Figure 4:
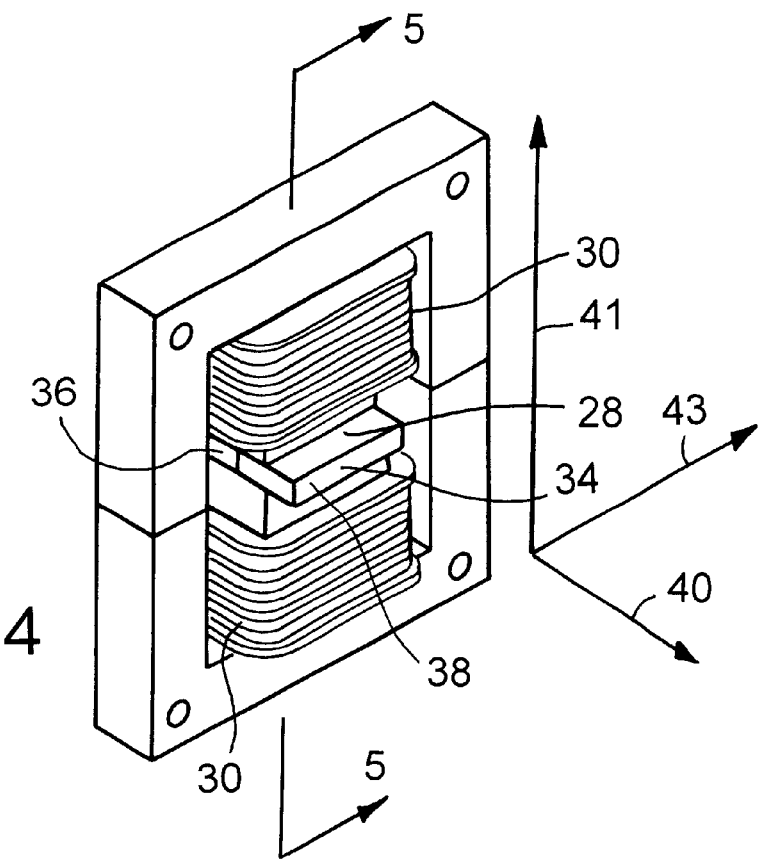
FIG. 4 is an isometric view of the core portion of FIG. 3 and a magnet assembly, positioned according to the invention.

Referring to FIG. 4, disposed in air gap 28 is permanent magnet assembly 34 which forms a portion of armature 14. Magnet sections 36 and 38 are discussed in the discussion of FIG. 5.

Figure 5:
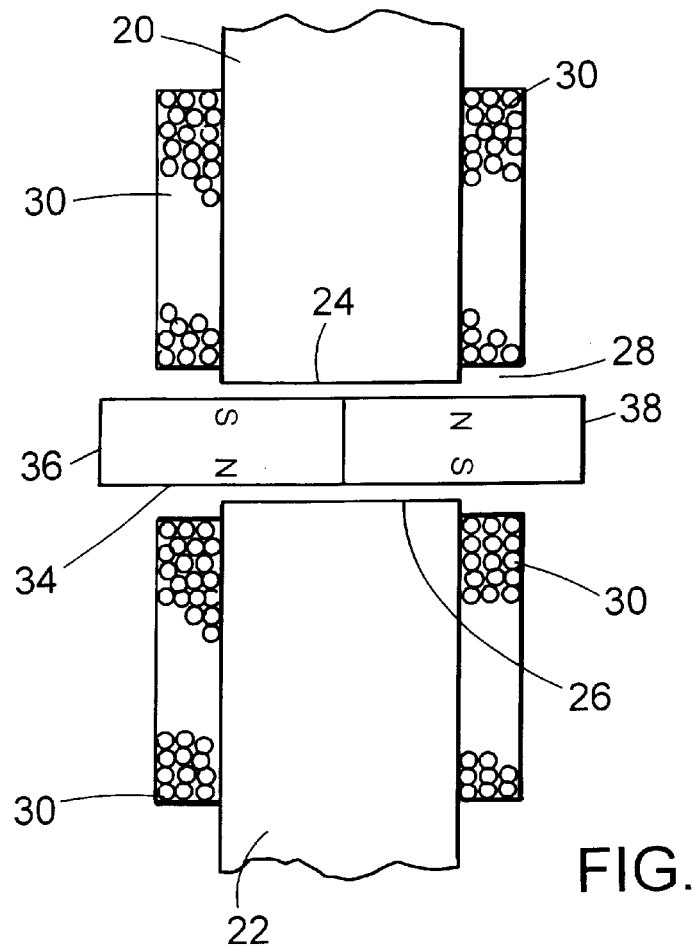
FIG. 5 is a cross-sectional view of the core portion and magnet assembly of FIG. 4.

Referring to FIG. 5, there is shown a cross section of the assembly of FIG. 3, taken along line 5—5 of FIG. 4. Magnet assembly 34 is divided into two section 36, 38 with alternating poles, disposed in and substantially filling air gap 28, and in noncontacting relation with faces 24, 26 of central core portions 20 and 22. Stator assembly 12 of FIG. 1, coils 30, and permanent magnet assembly 34 are elements of a permanent magnet transducer typically in accordance with U.S. Pat. No. 5,216,723, which also shows other topologies for core portion 13. In addition to the topologies shown in U.S. Pat. No. 5,216,723, other types of linear motors, such as described in U.S. Pat. No. 5,661,446, or tubular moving magnet linear motors can be used.

Referring again to FIG. 4, when electrical current flows through coils 30, permanent magnet assembly 34 moves in the direction of axis 40 (hereinafter the "motion axis"). When permanent magnet assembly 34 is centered between opposing faces 24 and 26, the magnetic forces in the direction of axis 41 between permanent magnet assembly 34 and the opposing faces balance, keeping the magnet assembly centered. However, if the magnet assembly becomes uncentered, the magnetic forces between the magnet assembly and opposing faces becomes unbalanced, and the magnet assembly is urged toward one of the opposing faces 24, 26 of FIG. 3, causing magnet assembly 34 to contact, or "crash" into, one or both of opposing faces 24, 26 of FIG. 3. This force, perpendicular to the intended motion of the permanent magnet assembly 34, and toward one of the opposing faces 24, 26 is referred to a "crashing force." The axis 41 perpendicular to the axis of motion and running between the opposing faces is referred to as the "crashing axis." In addition to an uncentered situation, other causes of crashing behavior may include misalignment of the suspension holding the permanent magnet assembly 34 and lack of parallelism between permanent magnet assembly 34 and the opposing faces 24, 26, and nonuniformity in the geometry of magnet assembly 34. For increased efficiency, however, it is desirable for permanent magnet assembly 34 to substantially fill air gap 28, and to remain in gap 28. There is minimal force acting along axis 43, which is perpendicular to axis of motion 40 and crashing axis 41. The parameters, therefore, for suspension element 16 are different along the three axes 40, 41, and 43. Along axis of motion 40, the suspension should allow motion but limit the range of motion along axis of motion 40 so that armature 14 remains in air gap 28. Along crashing axis 41, suspension element 16 should preferably be able to resist crashing forces. Along axis 43, the suspension element should limit motion, but does not need to resist strong forces.

Figure 6B:
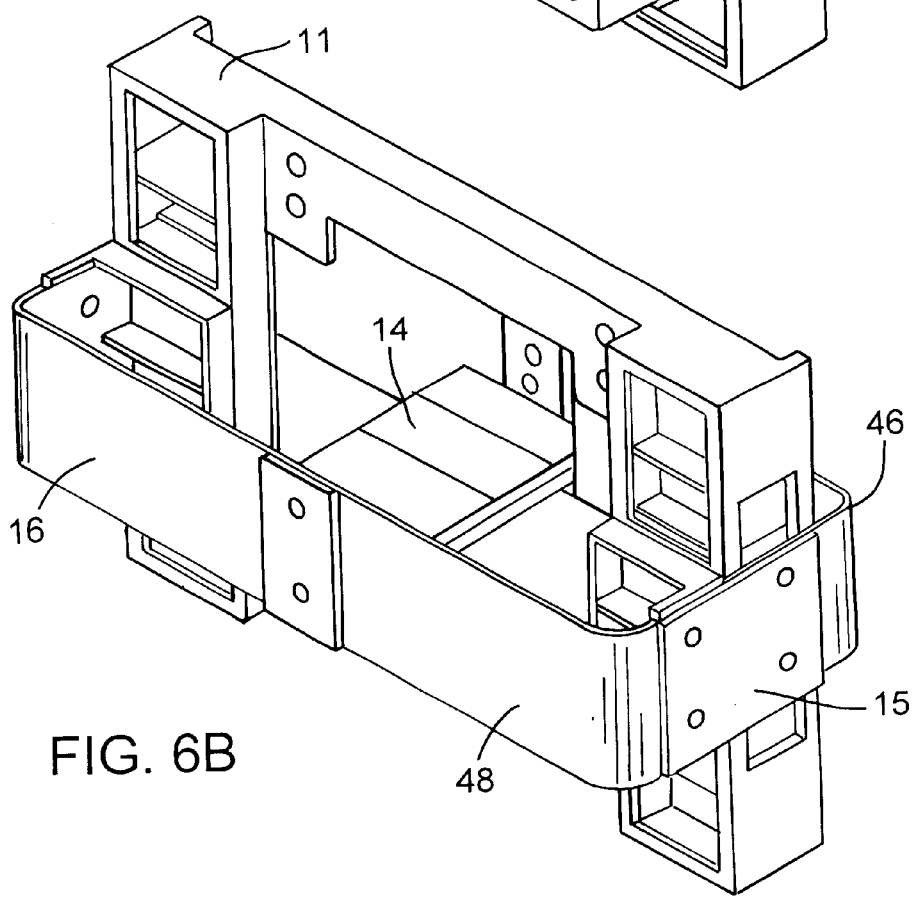
FIGS. 6a and 6b are isometric views of selected elements of the motor assembly of FIG. 2.
Figure 6A:
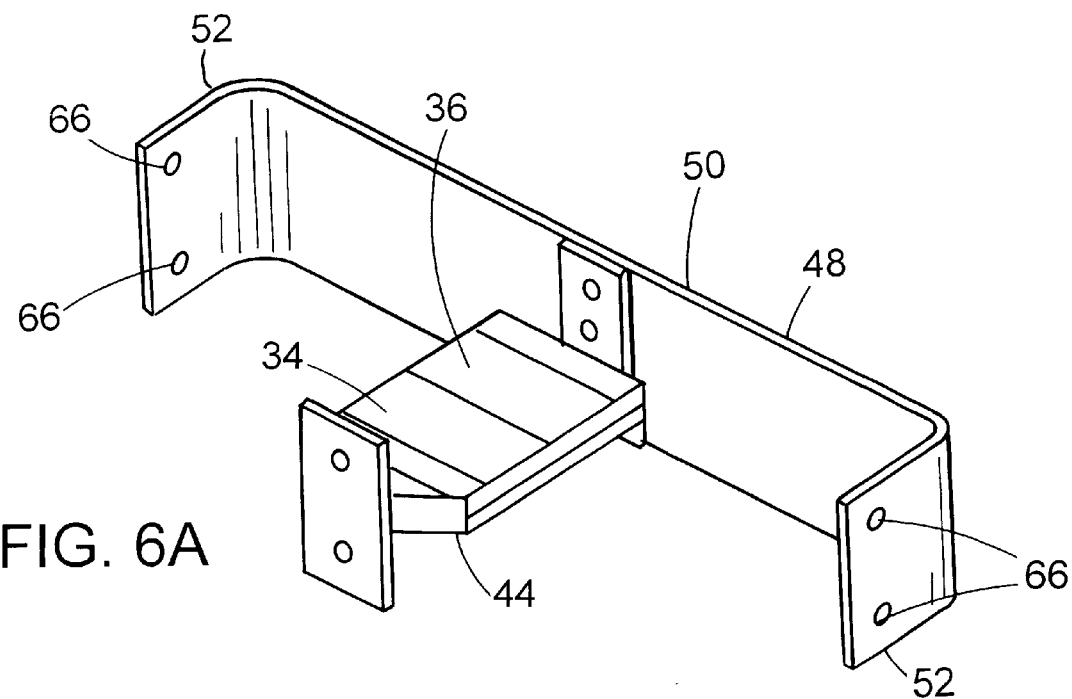

Referring to FIGS. 6a and 6b, there is shown the frame 11, frictionless flexural suspension system 16, and armature 14. For clarity, core portion 13 is not shown. Frictionless flexural suspension system 16 includes two flexure components 46, 48. Referring to FIG. 6a, armature 14 includes a carrier tray 44 for magnet sections 34, 36. Carrier tray 44 is attachable to flexure component 48 (and to flexure component 46, not shown). Flexure components 46, 48 may be formed of a band having a planar portion 50, with the ends 52 of the band bent so that they are approximately perpendicular to the plane of the planar portion. The ends 52 may be attached to frame 11 by multiple rivets through rivet holes 66. The rivets "sandwich" flexure components 46, 48 between pressure plate 15 of FIG. 6b and frame 11. The flexure components 46, 48 are oriented such that the plane of the band is perpendicular to motion axis 40 of FIGS. 3 and 4 of armature 14 and such that the band extends in a direction parallel to the crashing axis 41 of FIGS. 3 and 4, as shown in FIG. 6b.

Flexure components 46 and 48 control motion along all three axes 40, 41, 43 of FIG. 4. Flexure components 46, 48 flex to allow motion along axis 40. The flexing results in a restorative force along the axis of motion, to keep magnet sections 34, 36 in air gap 28. Flexure components 46, 48 are very rigid along crashing axis 41 to overcome crashing forces and prevent crashing behavior. Flexure components 46,48 are sufficiently rigid along axis 43, perpendicular to axis of motion 40 and crashing axis 41 to keep armature 14 in air gap 28.

If one or more of the causes of crashing behavior noted above is present, the crashing force is present even if there is no current flowing through the coil. Even if the magnet assembly is perfectly symmetric and centered in the gap, this only represents a "metastable" equilibrium position, analogous to a ball resting on the top of a very sharp, steep hill. Any external disturbance would send the ball to one side or another. In this ball analogy, gravity is the forcing function. In the case of the linear motor, the magnetic field is the forcing function. To center the magnet assembly in the gap against crashing forces, the magnet assembly is attached to a suspension system according to the invention as one method of achieving this result.

One method of estimating the centering force necessary is to assume that the total external mmf drop of the magnet is in the air gap (that is the central core portions are infinitely permeable). For a magnetic perturbation of 5% (interpreted as a +2.5% field variance at the top surface from the mean value and a −2.5% variance from the mean at the bottom surface, a magnetic pressure can be calculated by $P_m = B^2/2\mu_o$, where $\mu_o$ is $1.25 \times 10^{-6}$. A nominal value of 1.0 T can be assigned to B. An approximate pressure is thus $4 \times 10^5$ N/m² (60 psi). The differential pressure would be about $(4 B^* \Delta B)/2 \mu_o$ or a resulting pressure of $(4^*0.025^*1.)/2.5 \times 10^{-6}$, or $0.4 \times 10^5$ N/m². For the motor sizes on the order of sq. in. the (estimated) side force can be as high as 6 lbs. Tests on actual motors yielded crashing force measurements on the order of 0–5 lbs (0–22 N) for a geometrically centered magnet. By carefully displacing the magnets within the center of the air gap it was possible to determine that the magnetic-induced negative stiffness was on the order of 1,000 to 4,000 lbs/in, depending on the size of motor built (the bigger the motor the higher the crashing instability).

A suspension system that fulfills these requirements includes two flexure components 46, 48, of stainless steel such as Sandvik 7C27Mo2, of dimensions shown in FIG. 6b and having a thickness of 0.33 mm (0.012 inches). Other materials, such as other metals or molded or themoformed composites may be suitable.

Figure 7:
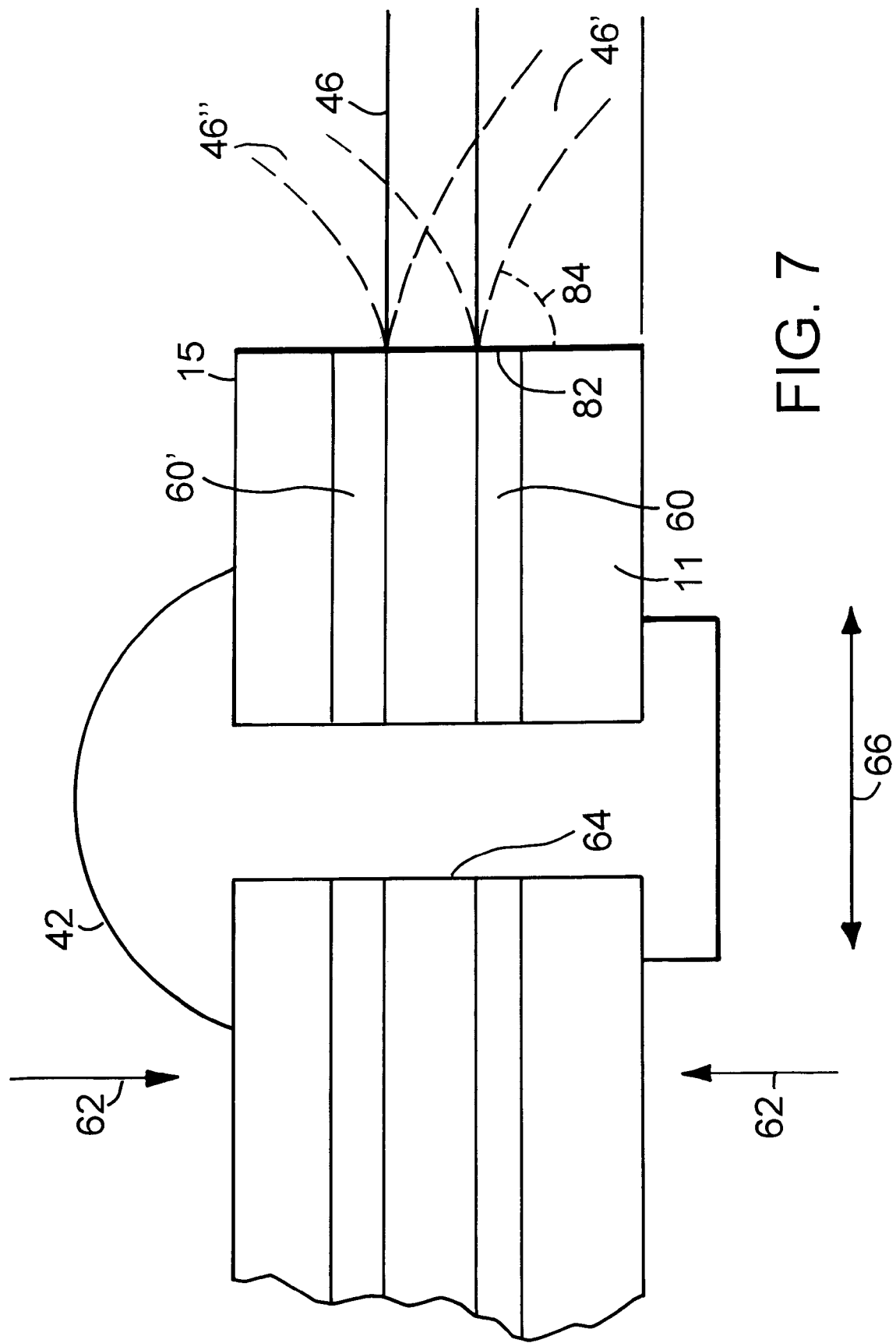
FIG. 7 is a cross-sectional view of the interface of selected elements of FIG. 2.

Referring now to FIG. 7, there is shown a cross section of the interface of one end of flexure component 46 and frame 11. Flexure component 46 is "sandwiched" between pressure plate 15 and frame 11. On the interfacing surfaces of frame 11 and flexure component 46 is a compliant layer 60 approximately 25–75μ thick of acrylic adhesive film having a modulus of elasticity in the range of 0.1 ms. Similarly, on the interfacing surfaces of flexure component 46 and pressure plate 15 is a similar compliant layer 60'. Rivet 42 holds the sandwich configuration in place, and applies force in the direction indicated by arrows 62, normal to the interfacing surfaces and to the layer of acrylic adhesive, thereby preloading compliant layers 60 and 60' and assisting in keeping the compliant layers in place. Rivet 42 is inserted in a manner such that it completely fills opening 64 in flexure component 46, thereby preventing any motion in the direction indicated by arrow 66. The other end of flexure component 46, end both ends of flexure component 48 are both coupled to frame 11 in the manner shown in FIG. 7.

Motion of the armature causes the flexure component 46 to deflect to positions such as indicated by 46' and 46". When flexure component 46 deflects toward frame 11 as in position 46', flexure component 46 is urged toward frame 11. Compliant layer 60 compresses so that it deforms from undeformed boundary 82 to deformed boundary 84, thereby preventing contact between frame 11 and flexure component 46. The preventing of contact between frame 11 and flexure component 46 greatly reduces the occurrence of fretting, which can be a significant source of wear and eventual failure of suspension systems that experience repetitive contact of elements made of dissimilar materials such as stainless steel flexure component 46 and frame 11, which may be made of a metal such as aluminum or a molded plastic.

When flexure component 46 is deflected to position 46", compliant layer 60' behaves in a manner similar to the compliant layer 60 as described in the above paragraph.

The invention may be practiced using other types of suspensions that operate without any sliding contact, such as air bearings, liquid bearings, and magnetic bearings. In an exemplary embodiment, flexure bearings are used because they are simpler and less expensive than other types of nonsliding contact bearings.

Suspension systems employing air bearings typically have a separate pump and associated "plumbing," fittings, and other components. Suspension systems employing fluid bearings are effective with fluid in the gap. Fluid bearings can remain indefinitely in the gap without the pumps or other components typically used with air bearings if the surface tension is sufficient to withstand the crashing force between magnet structure 34 and core faces 24, 26. The fluid pressure differential relative to ambient pressure is $\Delta P = \gamma / R$, where $\gamma$ = fluid surface tension N/m, R = fluid radius of the meniscus. (m).

The highest load from the magnet can be estimated to be 90 N (20 lbs) for the geometries presented, representative for the case in which the magnet is displaced off-center and rests against the pressure developed in the fluid layer. This results in a pressure, $P \sim 90N/(9.6 \times 10^{-4}) = 9 \times 10^4$ N/m$^2$. For a typical gap of 0.001' between the magnet structure and the core face, the required meniscus radius is one-half that clearance or 0.0005" ($1.3 \times 10^{-5}$ m). Using mercury (the fluid with exceptionally high surface tension) with a surface tension of 465 dyn/cm (0.465 N/m) results in a pressure differential, $\Delta P$, of $0.465/(0.0005/39)$, or $3.6 \times 10^4$ N/m$^2$. This is very close to the pressure required to maintain separation of the magnet structure from the core faces. The stiffness of such a bearing against crashing loads is about $$k_{dc} = 2\gamma(w*h)/g^2,$$
$$= 2*0.465*(3.2 \times 10^{-2} * 1.5 \times 10^{-2})/(1.3 \times 10^{-5})^2,$$
$$= 2.6 \text{ N/}\mu.$$

Other lubricants (oils, films) have surface tensions less than one-tenth that of mercury, and the gap is preferably reduced by at least a factor of 10. The damping forces (drag) would increase as the gap gets smaller, since $F_{drag}$=velocity*$\mu$A/g. For velocity~1 m/s, and the case of oil, ($\mu_f$, fluid viscosity of 100 cP, or 0.1 N-s/m$^2$, surface tension 32 dyn/cm or 0.03 N/m), the drag force is $1*(0.1)*(3.2\times10^{-2}*1.5\times10^{-2})/2.5\times10^{-6}$, resulting 15 N. The damping factor, would be 15 N-s/m.

So a suspension system employing a fluid film approach must have a small gap, but the size of the gap must be very precise, and the amount of precision required increases as the gap gets smaller. This represents a significant manufacturing challenge which makes materials testing system employing the invention cheaper and more reliable than materials testing systems employing fluid bearings.

It is evident that those skilled in the art may now make numerous modifications of and departures from the specific embodiments described herein without departing from the inventive concepts. Consequently, the invention is to be construed and limited only by the spirit and scope of the appended claims. Other embodiments are within the claims.

What is claimed is:

1. A materials testing device for applying force to a test specimen comprising:
   a linear motor comprising an armature assembly,
   said armature assembly mechanically coupleable to said test specimen;
   a stator assembly; and
   a suspension for supporting said armature and for controlling the motion of said armature relative to said stator assembly and to said test specimen, said suspension being arranged and constructed to operate without sliding contact between said armature assembly and said suspension.

2. A materials testing device in accordance with claim 1, wherein said suspension is a flexural suspension and includes a flexure component, said flexure component permitting a limited range of motion along a first axis and resisting motion along a second axis and a third axis.

3. A materials testing device in accordance with claim 2, said flexural suspension comprising a flexible band, said band having a planar portion, the plane of said planar portion being oriented substantially perpendicular to said first axis.

4. A materials testing device in accordance with claim 3, said flexible band having ends, said ends being bent relative to said planar portion so that the planes of said ends are substantially perpendicular to said plane of said planar portion and substantially parallel to said first axis.

5. A materials testing device in accordance with claim 2, said flexure component providing mechanical coupling of said armature assembly and said stator.

6. A materials testing device in accordance with claim 2, wherein said stator assembly and said flexural suspension are coupled along an interface surface, and wherein said interface surface is coated with a coating of a compliant material.

7. A materials testing device in accordance with claim 6, wherein said compliant material has a modulus of elasticity in the range of 0.1.

8. A materials testing device in accordance with claim 7, wherein said compliant material is an acrylic adhesive.

9. A materials testing device in accordance with claim 2 wherein said flexural suspension is arranged and constructed to operate essentially frictionlessly.

10. A materials testing device, comprising:
    a core of low reluctance magnetic material, said core having two mutually opposing faces;
    an air gap separating said mutually opposing faces;
    a coil wound on said core;
    a permanent magnet assembly in and substantially filling said air gap in noncontacting relationship with said core and constructed and arranged to have motion;
    a frictionless flexural suspension structure for supporting said permanent magnet assembly and for controlling the direction of motion of said permanent magnet assembly.

11. A materials testing device in accordance with claim 10, wherein said core and said permanent magnet assembly are mechanically coupled by said frictionless flexural suspension structure.

12. A materials testing device in accordance with claim 10, wherein said core and said flexural suspension are coupled along an interface surface, and wherein said interface surface is coated with a coating of a compliant material.

13. A materials testing device in accordance with claim 12, wherein said compliant material has a modulus of elasticity of approximately 0.1.

14. A materials testing device in accordance with claim 12, wherein said compliant material is an acrylic adhesive.

15. A materials testing device in accordance with claim 3 wherein said flexural suspension is designed arid constructed to operate essentially frictionlessly.

16. An electromechanical actuator assembly, comprising:
a structure of low reluctance material,
a coil wound on said structure, said structure having substantially planar opposing faces;
an air gap between said opposing faces;
a movable permanent magnet assembly, disposed in and substantially filling said air gap, said permanent magnet assembly having regions of opposite polarity;
said actuator assembly being characterized by three axes, a first of said axes perpendicular to said opposing faces, a second of said axes perpendicular to said first axis and between said regions of opposite polarity, a third of said axes perpendicular to said first axis and said second axis;
a substantially frictionless suspension assembly supporting said permanent magnet assembly, said suspension assembly having different stiffnesses along each of said three axes, wherein said suspension is stiffest along said first axis.

17. An electromechanical actuator, in accordance with claim 16, said suspension system comprising a flexure component.

18. A materials testing device in accordance with claim 17, said flexure component comprising a flexible band, said band having a planar portion, the plane of said planar portion being oriented substantially perpendicular to said first axis.

19. A materials testing device in accordance with claim 18, said flexible band having ends, said end being bent relative to said planar portion so that the plane of said ends is substantially perpendicular to said plane of said planar portion and substantially parallel to said second axis.

20. A materials testing device in accordance with claim 1 wherein said linear motor comprises,
a core of low reluctance magnetic material having two mutually opposing faces,
an air gap separating said mutually opposing faces,
a coil wound on said core,
a permanent magnet assembly in and substantially filling said air gap in noncontacting relationship with said core and constructed and arranged to have motion and comprising said armature assembly,
and a frictionless flexural suspension structure constructed and arranged for supporting said magnet assembly and for controlling the direction of motion of said permanent magnet assembly.

21. A materials testing device in accordance with claim 20 wherein said core and said permanent magnet assembly are mechanically coupled by said frictionless flexural suspension structure.

22. A materials testing device in accordance with claim 21 wherein said core and said frictionless flexural suspension structure are coupled along an interface surface that is coated with a coating of a compliant material.

23. A materials testing device in accordance with claim 22 wherein said compliant material has a modulus of elasticity of approximately 0.1.

24. A materials testing device in accordance with claim 22 wherein said compliant material is an acrylic adhesive.

25. A materials testing device in accordance with claim 20 wherein said linear motor is characterized by three axes, a first of said axes perpendicular to said mutually opposing faces, a second of said axes perpendicular to said first axis and between said regions of opposite polarity, and a third of said axes perpendicular to said first and second axes,
and said frictionless flexural suspension structure is characterized by different stiffnesses along each of said three axes with the stiffest stiffness being along said first axis.

* * * * *

UNITED STATES PATENT AND TRADEMARK OFFICE
CERTIFICATE OF CORRECTION

PATENT NO.      : 6,405,599 B1
DATED           : June 18, 2002
INVENTOR(S)     : Paul J. Patt It is certified that error appears in the above-identified patent and that said Letters Patent is hereby corrected as shown below:

<u>Column 7,</u>
Line 32, "A materials testing device" should read -- An electromechanical actuator --.
Line 36, "a material testing device" should read -- An electromechanical actuator --.

Signed and Sealed this

Second Day of December, 2003

JAMES E. ROGAN
*Director of the United States Patent and Trademark Office*